(12) United States Patent
Turchetta et al.

(10) Patent No.: US 7,417,149 B2
(45) Date of Patent: Aug. 26, 2008

(54) PROCESS FOR THE PREPARATION OF MONTELUKAST

(75) Inventors: Stefano Turchetta, Rome (IT); Angela Tuozzi, Rome (IT); Elio Ullucci, Latina (IT); Lorenzo De Ferra, Rome (IT)

(73) Assignee: Chemi SpA, Milan (IT)

( * ) Notice: Subject to any disclaimer, the term of this patent is extended or adjusted under 35 U.S.C. 154(b) by 0 days.

(21) Appl. No.: 11/346,574

(22) Filed: Feb. 3, 2006

(65) Prior Publication Data

US 2006/0194839 A1 Aug. 31, 2006

(30) Foreign Application Priority Data

Feb. 18, 2005 (IT) .......................... MI2005A0247

(51) Int. Cl.
*C07D 215/18* (2006.01)
(52) U.S. Cl. ..................................................... 546/174
(58) Field of Classification Search ................. 514/311; 546/180, 174
See application file for complete search history.

(56) References Cited

U.S. PATENT DOCUMENTS

| 5,565,473 | A | 10/1996 | Belley et al. |
| 6,320,052 | B1 * | 11/2001 | Bhupathy et al. ........... 546/174 |
| 2005/0107612 | A1 | 5/2005 | Reguri et al. |

FOREIGN PATENT DOCUMENTS

| EP | 0 500 360 A1 | 8/1992 |
| EP | 500360 A1 * | 8/1992 |
| WO | WO 98/39970 | 9/1998 |
| WO | WO 2004/108769 A2 | 12/2004 |
| WO | WO 2006/008571 A1 | 1/2006 |

OTHER PUBLICATIONS

Dufresne et al., Synthesis of Montelukast (MK-0476) Metabolic Oxydation Products, J. Org. Chem., 1996, 61, 8518-8525.*
Wang, D., et al; "Process for the preparation of montelukast sodium and its intermediate"; *Caplus*; 2001, 6 pages; XP-002343618.
King, A.O., et al; "An Efficient Synthesis of LTD Antagonist L-699,392"; *J. Org. Chem.*; 1993, vol. 58; pp. 3731-3735.

* cited by examiner

*Primary Examiner*—Bernard Dentz
*Assistant Examiner*—David E Gallis
(74) *Attorney, Agent, or Firm*—Nixon & Vanderhye

(57) ABSTRACT

The present invention relates to a process for the preparation of Montelukast and the salts thereof comprising the following steps:

(a) reaction of a compound A with a compound A2 in which n varies between 1 and 2 and, when n is 1, R is methyl and, when n is 2, R is a $C_1$-$C_4$ alkyl or an aryl, and X is a leaving group, by nucleophilic substitution reactions in dipolar organic solvents to yield the compound A3

(b) reaction of the compound A3 with an inorganic acid HY, in which Y is Cl, Br, I, and subsequent isolation of the resultant salt A4;

(c) optional conversion of the salt A4 into the compound A3;
(d) methylation of the salt A4 and/or of the compound A3 to yield Montelukast.

31 Claims, 4 Drawing Sheets

PROCESS FOR THE PREPARATION OF MONTELUKAST

The present invention relates to a novel method for the preparation of Montelukast acid and the salts thereof which makes it possible to achieve an improvement in terms of yields and purity of the final product relative to existing methods.

FIELD OF THE INVENTION

Montelukast sodium salt, or the sodium salt of [R-(E)]-1-[1-[3-[2-(7-chloro-2-quinolinylethenyl]phenyl]-3-[2-[(1-hydroxy-2-methylethyl)phenyl]propyl]thio]methyl]cyclopropaneacetic acid, the structural formula of which is shown below,

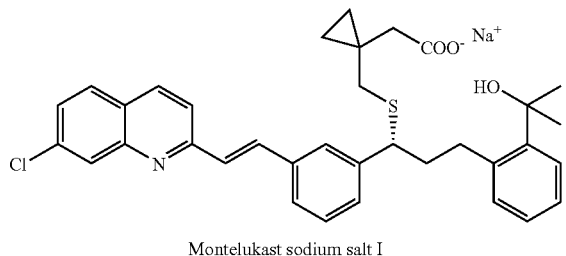

Montelukast sodium salt I is a powerful and selective inhibitor of the synthesis of leucotrienes, which are endogenous substances responsible for the development of inflammatory conditions, such as asthma, pulmonary diseases, allergic rhinitis, etc.

The synthesis of Montelukast sodium salt (I) in amorphous form is described in U.S. Pat. No. 5,565,473 and provides the independent synthesis of two subunits II and III which are combined in the final stage of the process to form (IV) according to the scheme shown in FIG. 1.

The protected mesylate (II) is reacted with the ester (III) in the presence of bases such as $Cs_2CO_3$ or hydrides to yield the protected ester alcohol IV. After deprotection, the ester V is hydrolysed to form the acid VI and then converted directly to the sodium salt (I). Both the methyl ester V and the acid VI are subjected to chromatographic purification. The process is thus not suited to large scale production.

U.S. Pat. No. 5,614,632, on the other hand, describes a process for the synthesis of Montelukast sodium salt in crystalline form according to the scheme shown in FIG. 2. The method involves converting 1-mercaptomethylcyclopropaneacetic acid IIIa into the dilithium salt thereof by means of reaction with a lithium base, typically n-BuLi, in the presence of an inert solvent such as THF or toluene and then reacting said dianion with the mesylate IIa derived from the diol X.

This reaction gives rise to Montelukast acid VI, which is then purified by means of transformation into the dicyclohexylammonium salt (DCHA) (VII) and then converted into Montelukast sodium salt (I). The method in question does, however, exhibit a series of disadvantages.

First of all, the mesylate IIa exhibits elevated instability with regard to temperature, air and light; it is in fact prepared by selective monomesylation of the corresponding diol (X) at temperatures of between −15° C. and −10° C., under an inert atmosphere in a mixture of acetonitrile/toluene from which it precipitates at the end of the reaction. The product is then filtered out under nitrogen at −25° C., washed with acetonitrile at −30° C. and then with hexane at +5° C. It is finally dried at +5° C. under a stream of nitrogen for 20 h. It is thus obvious that all these procedures entail the use of techniques which are costly and cannot be directly applied industrially.

The mesylate IIa is then reacted with the dilithium salt of 1-(mercaptomethyl)cyclopropaneacetic acid (IIIa) in THF at temperatures of −10 to −5° C. The reaction mixture is heterogeneous and long reaction times are thus required (generally of 12 to 24 h) in order to achieve sufficient conversion.

Finally, despite the said method specifying controlled operating conditions, a product (Montelukast acid) (VI) is nevertheless obtained in crude form which requires subsequent purification. The product is in fact transformed into the corresponding dicyclohexylammonium salt (VII).

It may be learnt from U.S. Pat. No. 6,320,052 that the purification of (VI) as the dicyclohexylammonium salt is also a long and difficult process: dicyclohexylamine (DCHA) is added to the solution of the acid in ethyl acetate or toluene; crystals of Montelukast DCHA salt (VII) are necessary in order to promote crystallisation and the mixture is left to stand overnight at 20° C. The product must be obtained with a purity of greater than 99% and, if this is not the case, it is subjected to further crystallisation with a consequent inevitable loss of yield and increased process costs.

Montelukast DCHA salt (VII) is then in turn converted into the acid form thereof by treatment with a dilute solution of a weak acid. This step is somewhat delicate because, during the acidification phase of Montelukast DCHA salt (VII) to form the free acid, impurities may be formed, such as for example the unsaturated compound IX shown below,

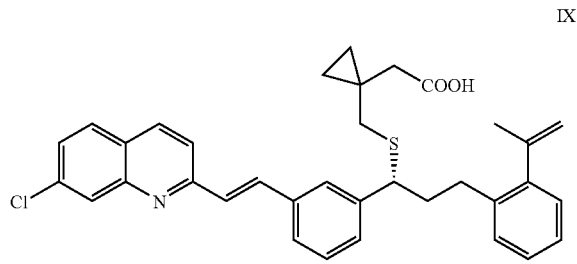

an impurity which is derived from dehydration of the tertiary alcohol group and is then difficult to remove.

Montelukast acid (VI) is then transformed into the sodium salt (I) by treatment with an alcoholic solution of sodium hydroxide. In this case too, it is difficult to achieve the formation of crystals and it is thus necessary to seed the mixture with crystallisation nuclei. The precipitate is left to stand at 40° C. for 2 h to allow the crystals to consolidate. Precipitation is then completed by adding acetonitrile in 2 aliquots, at an interval of 2 h from one another, and maintaining the temperature at 40° C. The mixture is finally left to stand at 40° C. for 12 h. As is clear from the above discussion, all known processes for obtaining Montelukast sodium salt (I) suffer serious disadvantages: long reaction times, instability of the intermediates, long and difficult purification processes. There is thus an obvious need to find an efficient method for the synthesis of Montelukast and the salts thereof which overcomes the problems associated with the prior art.

SUBJECT MATTER OF THE INVENTION

The primary object of the present invention is to provide an innovative process which makes it possible to obtain Montelukast acid and the salts thereof in elevated yields and at high purity.

During our investigations, we have surprisingly found that reacting a subunit A2 (synthesised starting from A1) with a subunit A makes it possible to obtain the product A3 in very good yield which, in comparison with VI, does not exhibit the disadvantage of intrinsic instability with regard to dehydration. A3 does not in fact comprise tertiary hydroxyls and thus cannot enter into elimination reactions which would give rise to the impurity IX.

A3 may be transformed into Montelukast acid VI by means of selective methylation of the $CO_nR$ function (in which, when n=1, R=$CH_3$; when n=2, R=alkyl, aryl) as shown in the scheme shown in FIG. 3. It has in fact been found that it is possible to cause the $CO_nR$ group to react selectively despite the presence of the potentially reactive $CO_2H$ group in the molecule.

Another aspect of the present invention is that the product A3 may be purified by transforming it, for example, into the hydrochloride and crystallising the latter. In this manner, the product A4 is obtained in elevated yield with a purity of ≧99%.

In the course of experimentation on A3, it has furthermore surprisingly been found that the methylation reaction of the $CO_nR$ group may also be performed efficiently on the corresponding salt A4, without it being necessary to deblock it to form the free base, with a consequent reduction in the number of steps and thus simplification of the process which leads to Montelukast sodium salt as in the scheme shown in FIG. 4.

Another aspect of the present invention resides in the possibility of transforming the hydroxyl group of A1 into a good leaving group at a temperature of between 0 and 20° C. The corresponding reaction is known in the literature, performed on the diol X, but requires temperatures of below 0° C. due to the instability of the product.

A2 may also be reacted with A both after having been isolated in crystalline form and as a crude product without requiring a specific isolation step.

Another aspect of the present invention involves the coupling reaction between the intermediate A2 and the cyclopropyl unit A. The reaction may be performed in dipolar aprotic solvents or in solvents such as tetrahydrofuran (THF), methyltetrahydrofuran, toluene etc., or in mixtures thereof. In particular, the best results are obtained in the presence of dipolar aprotic solvents because the reaction mixture is homogeneous and reaction times are thus reduced relative to those described for analogous reactions in the prior art (2-4 h vs. 15 h) (c.f. U.S. Pat. No. 6,320,052).

Another aspect of the present invention is the use of lithium hexamethyldisilazide instead of BuLi as the base for generating the dianion of 1-(mercaptomethyl)cyclopropaneacetic acid with a consequent reduction in risks from the standpoint of scability to industrial scale. BuLi, like all alkyllithium compounds in general, is in fact extremely flammable; moreover, given that alkyllithium compounds, apart from being strong bases, are also excellent alkylating agents if present in excess in the lithiation reaction of A, they can give rise to the formation of unwanted secondary products derived, for example, from nucleophilic attack by the alkyllithium on the $CO_nR$ function of A2 Lithium hexamethyldisilazide in contrast does not exhibit these disadvantages.

Another aspect of the present invention consists in having found a simple and convenient method for the purification and isolation of Montelukast acid (VI). The acid VI may, in fact, be purified by being suspended at temperatures of between 20 and 30° C. in a linear or branched alcoholic solvent. A product with a purity of ≧99.5% is thus obtained which is then transformed into the sodium salt by treatment with an aqueous alcoholic solution of sodium ions as described in U.S. Pat. No. 5,565,473.

The principle aspects of the present invention may accordingly be summarised as follows:
 i) transformation of the hydroxyl of compound A1 into a good leaving group by means of reaction with an alkyl or arylsulfonate performed at temperatures of between 0 and 20° C. in an apolar solvent in order to obtain the product A2;
 ii) formation of the dilithium salt (A) of 1-(mercaptomethyl)cyclopropaneacetic acid with lithium hexamethyldisilazide;
 iii) reaction of said dianion (A) with A2;
 iv) isolation and purification of A3 so obtained by means of transformation into the corresponding salt of an organic or inorganic acid of the formula A4;
 v) methylation alternatively of A3 or A4;
 vi) isolation and purification of Montelukast acid (VI) by precipitation with alcoholic solvents.

DESCRIPTION OF THE INVENTION

According to aspect (i) of the present invention, the compound A2 is prepared by reacting A1 with an alkyl or arylsulfonyl halide, preferably mesyl chloride, in an inert solvent such as toluene or dichloromethane, in the presence of an amine such as diisopropylethylamine (DIPEA), triethylamine (TEA) or dimethylaminopyridine (DMAP). The reaction is performed at between 0 and 20° C. for approx 2 h.

Compound A1may, in turn, be prepared according to known prior art processes, such as for example the process described in J.O.C. (1993), 58, 3731-3735, which is incorporated by reference.

According to aspect (ii), the dianion (A) is prepared by dissolving the cyclopropyl unit IIIa in an dipolar aprotic solvent, preferably DMF, DMA, DMSO, DMPU, more typically DMF, and adding to the resultant solution lithium hexamethyldisilazide dissolved in a solvent such as for example THF or methyl-THF, at a temperature of between 0° C. and 5° C., or by dissolving IIIa in a solvent such as for example THF or methyl-THF and adding a solution of lithium hexamethyldisilazide for example in THF.

According to aspect (iii), coupling between the dilithium salt of unit IIIa and the mesylate A2 is performed in a dipolar aprotic solvent such as DMF, DMA, DMSO, N-methylpyrrolidone, preferably DMF, or in a solvent such as THF or methyl-THF or in mixtures thereof. The mesylate A2, is added as a solid or in solution to the solution of the dianion (A), formed as described in point (ii). The reaction is performed at 0-5° C. for a period of 2-4 h.

Three methods have been developed for the purposes of purification of the product A3 as a hydrochloride, (point iv):

METHOD 1: After aqueous working up, the product A3 derived from the coupling reaction is extracted with an apolar solvent, typically toluene. A solution of HCl in a ketone solvent, such as acetone, methyl ethyl ketone, methyl isobutyl ketone, preferably acetone, is added to the toluene solution. The product is isolated by filtration at a temperature of between 0 and 20° C., preferably between 10 and 15° C.

The product exhibits HPLC purity of 97-99%.

METHOD 2: The product A3 derived from the coupling reaction, is extracted with a low-boiling, concentrated chlorinated solvent. The residue is dissolved in a ketone solvent, typically acetone. A solution of gaseous HCl in an apolar solvent, typically toluene, is added to the solution. The product is isolated by filtration at 0-20° C., preferably between 10 and 15° C., and exhibits HPLC purity of 97-99%.

METHOD 3: The product A3 derived from the coupling reaction is extracted in an apolar solvent, preferably toluene, a ketone solvent, typically acetone, is added to the solution and gaseous HCl is bubbled into the resultant solution at a temperature of between 0 and 20° C. The product is isolated by filtration and exhibits HPLC purity of 97-99%.

According to aspect (v) of the present invention, the product A3 is selectively methylated in position $CO_nR$ despite the presence of a carboxy function. In general, where n=2, R=alkyl, aryl, the reaction is performed in an in inert solvent, for example THF, with MeMgCl, which has previously been activated with a cerium salt, typically $CeCl_3$. The reaction may be performed both on the intermediate $A_3$ as such and on its hydrochloride $A_4$. The $CeCl_3$ is refluxed in THF for 2-18 h, preferably 3-4 h, and then cooled to 0° C. The magnesium compound is then added (between 5 and 10 moles relative to $A_3$, preferably between 5 and 6). Finally, A3 dissolved in THF, or the hydrochloride $A_4$ suspended in the same solvent is added. The reaction is performed at a temperature of between 0 and 5° C. for 2-4 h. Montelukast acid (VI) is obtained without the formation of further secondary products.

In general, where n=1, R=$CH_3$, the reaction may also be performed in the absence of $CeCl_3$.

According to aspect (vi), Montelukast acid VI is isolated by suspending the product in a linear or branched alcoholic solvent at temperatures of between 20-30° C. and then performing filtration. A product with HPLC purity of ≧99.5% is obtained.

Montelukast acid is then transformed into the corresponding sodium salt and freeze-dried as described in U.S. Pat. No. 5,565,473.

To summarise, the present invention provides a process for the preparation of Montelukast or the pharmaceutically acceptable salts thereof comprising the following steps:

(a) reaction of a compound A

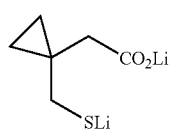

A with a compound A2

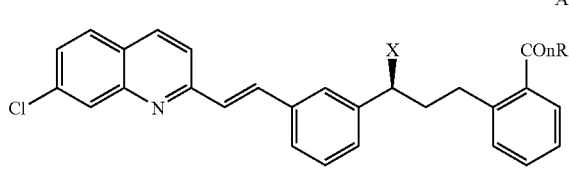

A2 in which n varies between 1 and 2 and, when n is 1, R is methyl and, when n is 2, R is a $C_1$-$C_4$ alkyl or an aryl, and X is a leaving group, by nucleophilic substitution reactions in dipolar organic solvents to yield the compound A3

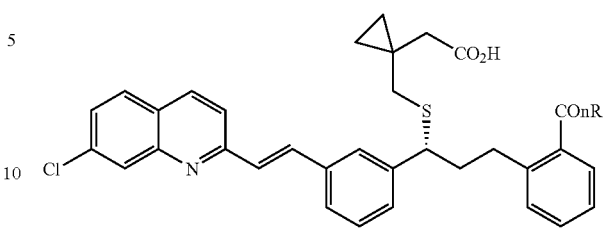

A3 in which n and R have the above-stated meanings;
(b) reaction of the compound A3 with an inorganic acid HY, in which Y is Cl, Br, I, and subsequent isolation of the resultant salt A4;

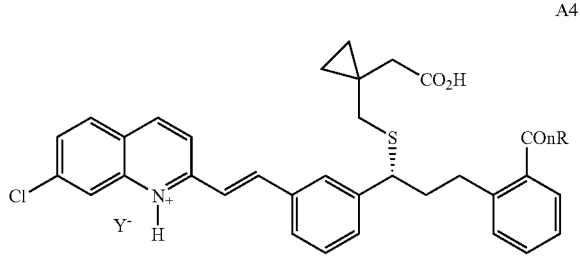

A4

(c) optional conversion of the salt A4 into the compound A3;
(d) methylation of the salt A4 and/or of the compound A3 to yield Montelukast.

The leaving group X may be selected from among $C_1$-$C_4$ alkylsulfonate, preferably methanesulfonate, and arylsulfonate.

Step (a) may be performed in a dipolar aprotic solvent or in a mixture of a dipolar aprotic solvent and an ethereal solvent. The dipolar aprotic solvent may be selected from among DMF, DMA, DMSO, DMPU, N-methylpyrrolidone; the mixture of dipolar aprotic solvent and ethereal solvent preferably consists of DMF and THF. The reaction temperature is normally between 0° C. and 5° C.

Step (b) is readily performed in an apolar or ketone solvent or in mixtures thereof, preferably toluene/acetone, at a temperature of between 20° C. and 10° C. The acid HY may be selected from among HCl, HBr and HI.

Step (d) is readily performed in an ethereal solvent, preferably THF; the reaction is preferably performed with MeMgCl in the presence of cerium salts, preferably $CeCl_3$, at a temperature of between 0 and 5° C.

The salt A4 may be purified by crystallisation in an apolar or ketone solvent or in mixture of the two, in which said apolar solvent is toluene and/or said ketone solvent is acetone. Conversion of the salt $A_4$ into the compound $A_3$ may be performed in an aqueous or aqueous alcoholic solvent, preferably at a pH of between 3 and 7.

The Montelukast may then be purified by pulping in an alcoholic solvent, preferably BuOH, s-BuOH and/or iso-BuOH.

The compound A may be obtained by reaction between 1-(mercaptomethyl)cyclopropaneacetic acid and lithium hexamethyldisilazide. Compound A2, on the other hand, may be obtained by reaction between compound A1 and a $C_1$-$C_4$ alkylsulfonyl halide, preferably mesyl chloride, or an arylsulfonyl halide. The reaction is preferably performed at 0-20° C. in an inert organic solvent, preferably selected from among toluene and dichloromethane, in the presence of a tertiary amine, preferably selected from among triethylamine, diisopropylethylamine and dimethylaminopyridine.

The invention additionally provides the intermediates A2, A3 and A4 and the use thereof in the preparation of Montelukast.

BRIEF DESCRIPTION OF THE DRAWINGS

The invention will now be further described with reference to the accompanying drawings, which.

Figure 1:
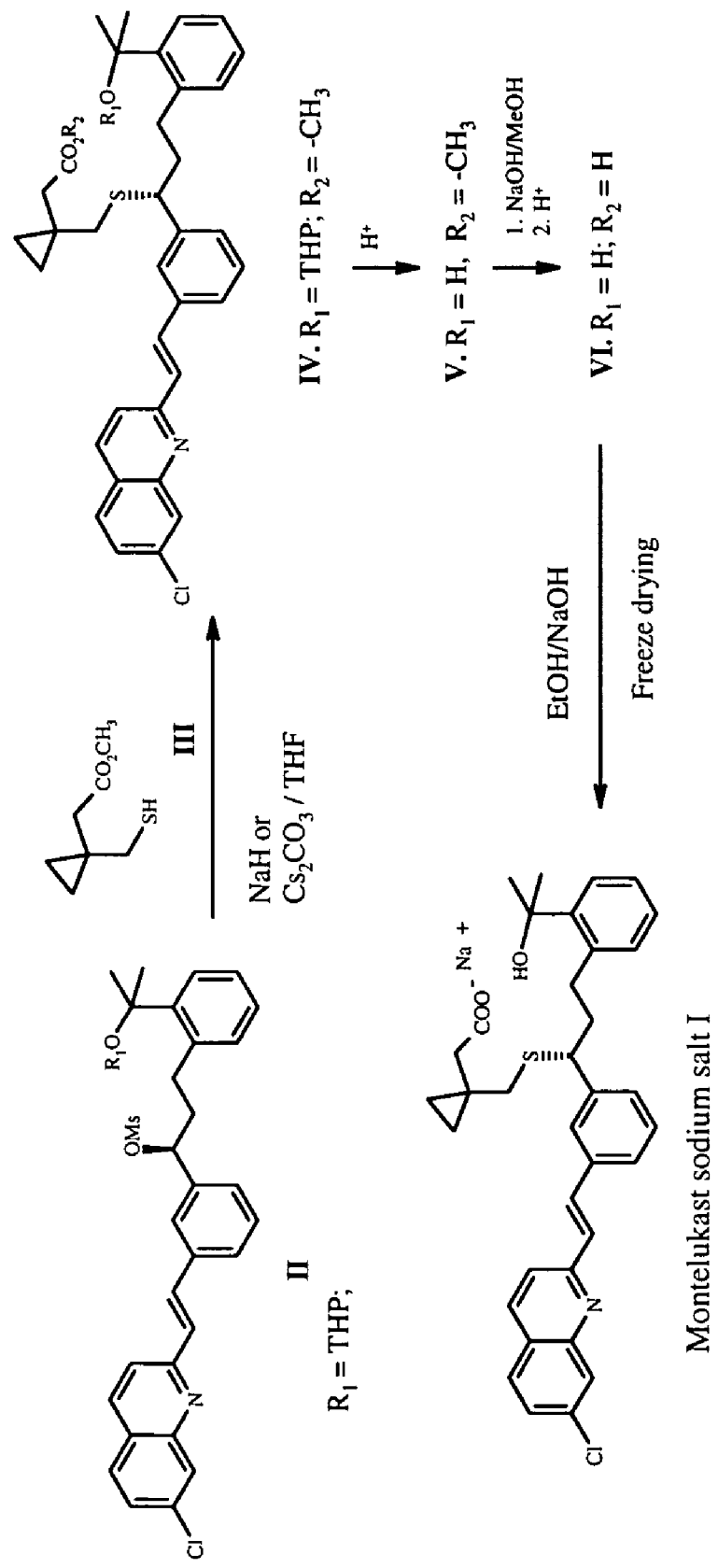
FIG. 1 is a schematic illustrating the reaction of two subunits II and III in the final stage of the process to form (IV)
Figure 2:
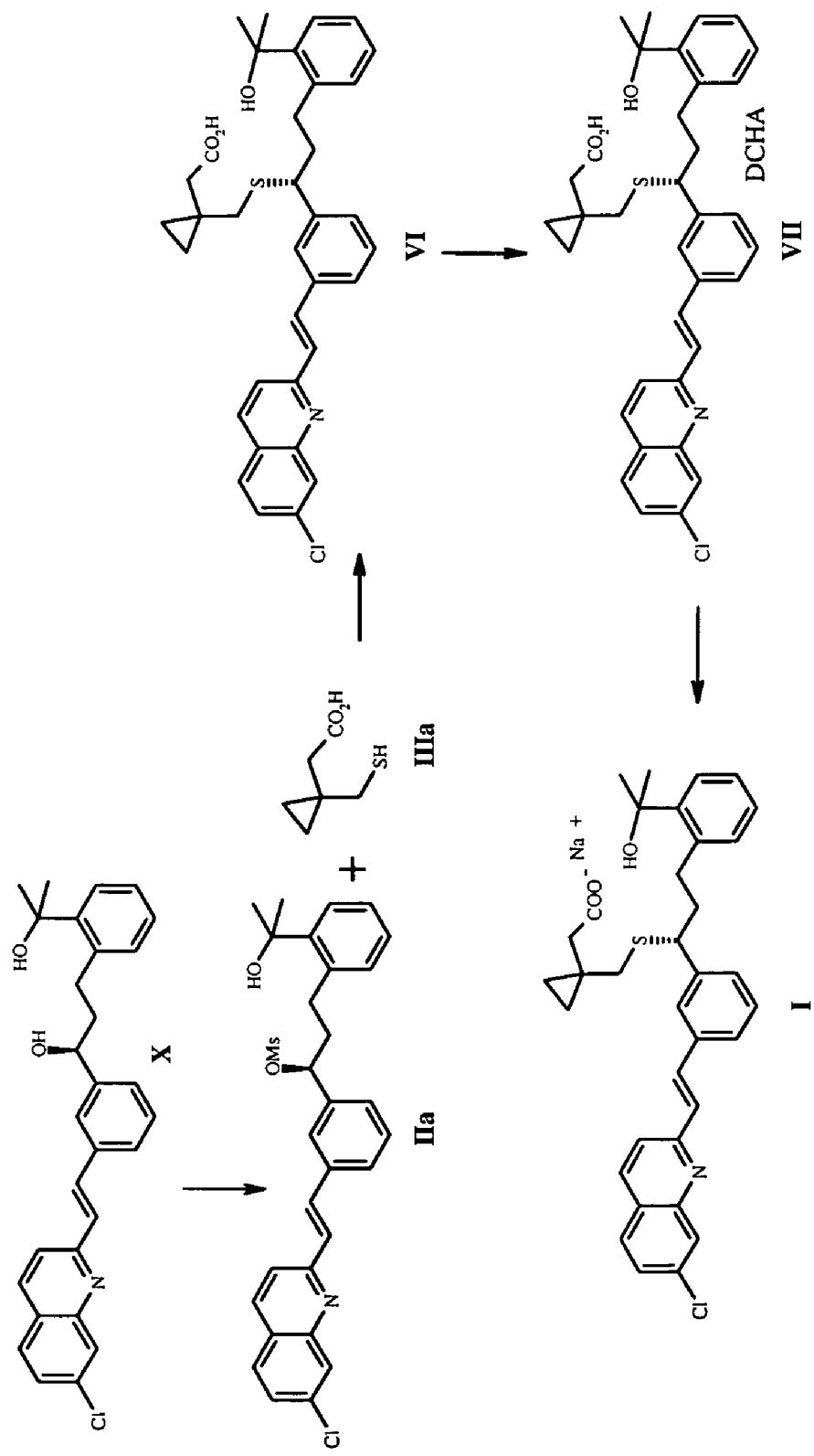
FIG. 2 is a schematic illustrating the process for the synthesis of Montelukast sodium salt in crystalline form.
Figure 3:
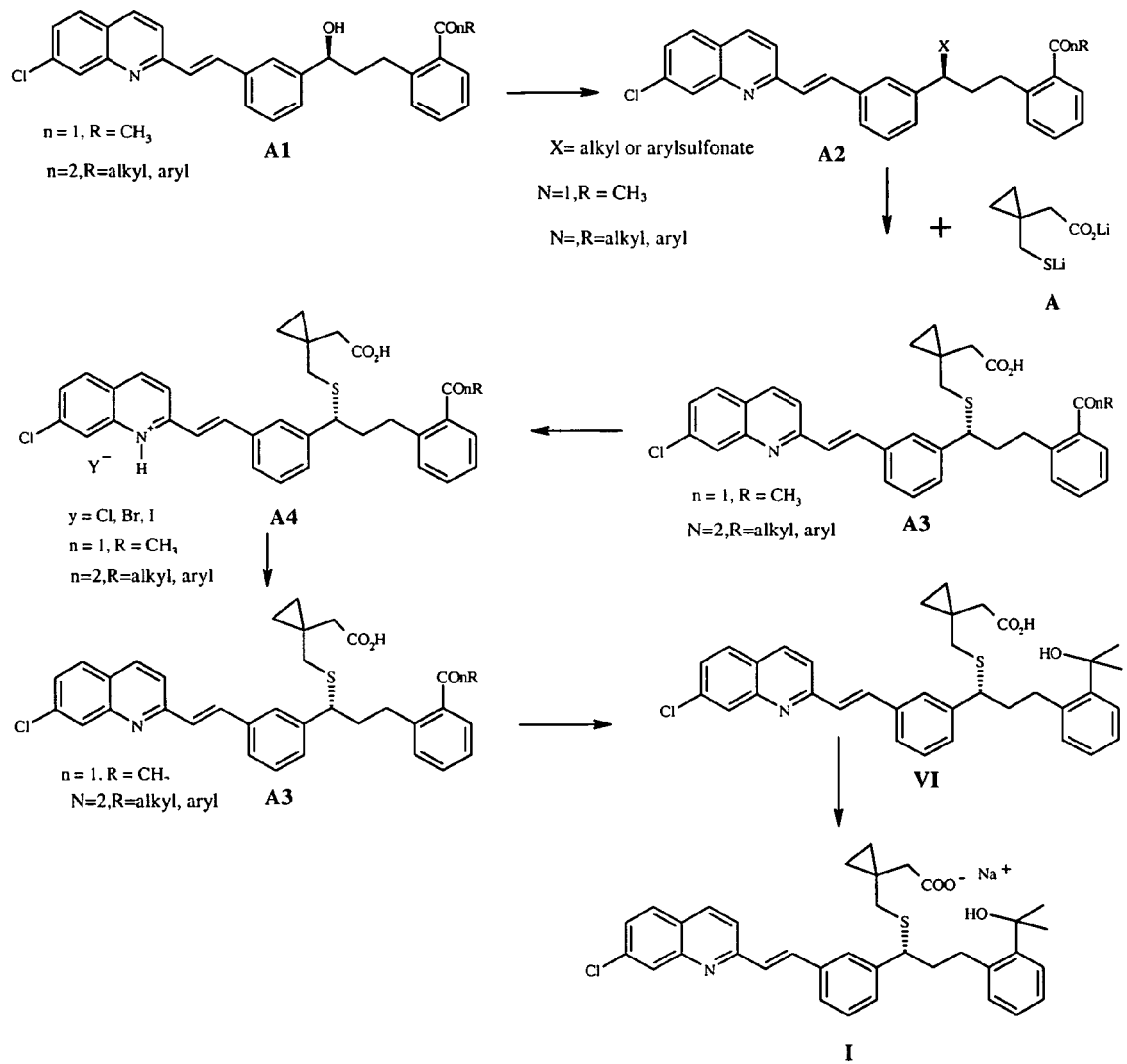
FIG. 3 is a schematic illustrating A3 being transformed into Montelukast acid VI by means of selective methylation of the $CON_nR$ function.
Figure 4:
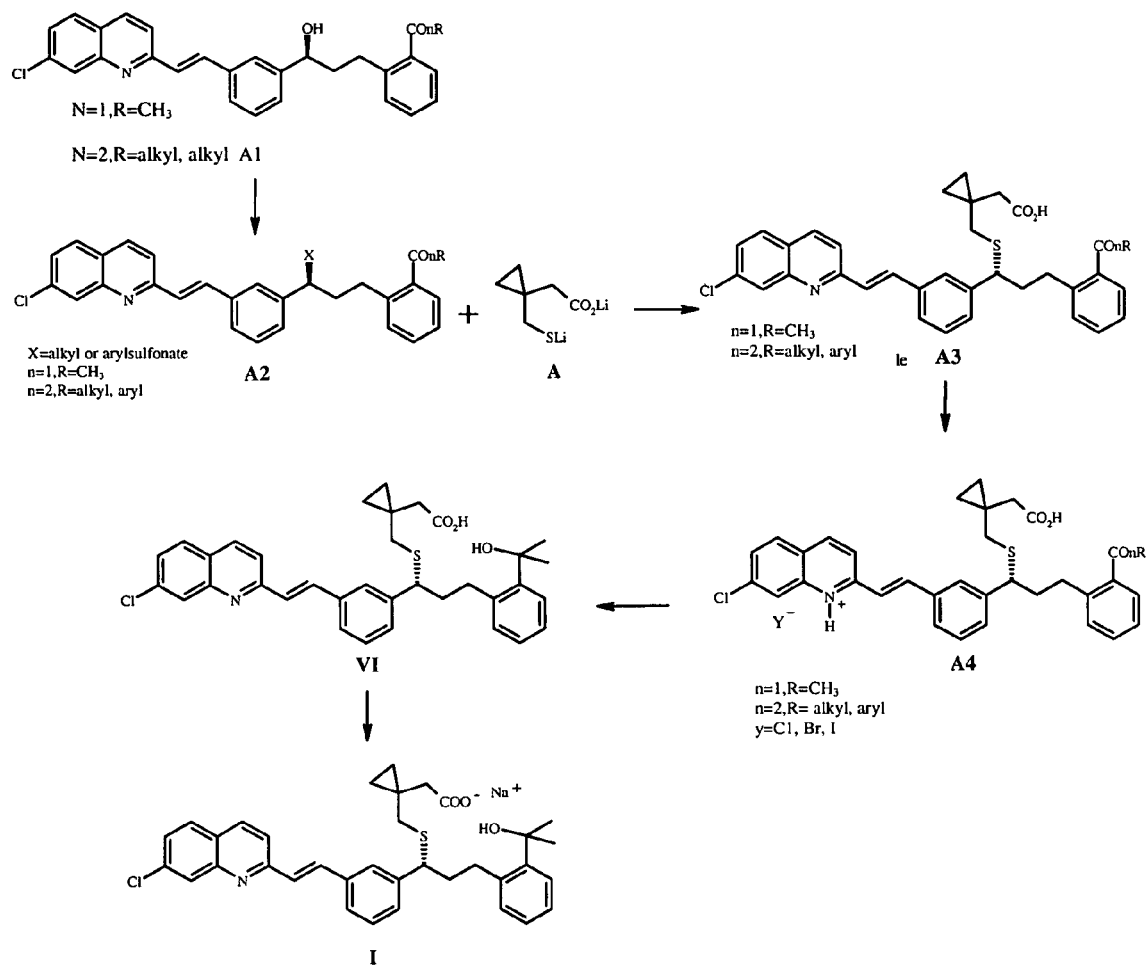
FIG. 4 is a schematic illustrating simplification of the process leading to Montelukast sodium salt.

The following Examples illustrate the present invention in greater detail and do not in any way limit the actual scope of the invention as specified in the claims.

EXAMPLE 1

Methyl [S-(E)]-2-[3-[3-[2-(7-chloro-2-quinolinyl) ethenyl]phenyl]-3-methanesulfonyloxy-propyl]benzoate (A2)

A 1 liter flask, fitted with a mechanical stirrer, a thermometer and a distillation head, was flushed with $N_2$. 42 g (0.088 moles) of hydroxy methyl ester monohydrate $A_1$, 1.06 g of DMAP (0.0088 moles) and 400 ml of sec.-butanol were then introduced into the flask. The suspension was heated to reflux and the $H_2O$-s-BuOH azeotropic mixture was removed by distillation at atmospheric pressure (200 ml). 400 ml of toluene were added to the bottom's residue and the s-BuOH was removed by distillation at atmospheric pressure (200 ml).

The solution was then cooled to −5° C. and triethylamine (27 ml, 0.194 moles) and mesyl chloride (18.14 g, 0.158 moles) were added in 20 minutes while keeping the internal temperature ≦0° C.

Once addition was complete, the solution was heated to 20° C. and kept at this temperature for 2 h. Once this time had elapsed, the reaction mixture was quenched by being poured into 500 ml of a saturated aqueous solution of $NaHCO_3$ at 5-10° C. The phases were separated and the organic phase was washed with 500 ml of a saturated solution of $NaHCO_3$ and then concentrated under a vacuum.

$^1$H-NMR(CDCl$_3$): ppm 8.2-7.1 (m, 15 H); 5.65 (t, 1H); 3.85 (s, 3H); 3.2-3 (m, 2H); 2.7 (s, 3H); 2.5-2.2 (m, 2H).

EXAMPLE 2

[R-(E)]-2-[3-[3-[2-(7-chloro-2-quinolinyl)ethenyl] phenyl]-3-(2-benzyloxy -methyl)propyl)thiomethyl-cyclopropaneacetic acid (A3)

21.2 g (0.145 moles) of 1-(mercaptomethyl)cyclopropaneacetic acid and 140 ml of DMF were introduced into a 1 liter flask equipped with a mechanical stirrer, a thermometer and a dropping funnel. The mixture was stirred at ambient temperature for 5 minutes in order to ensure complete dissolution and was then cooled to 0-5° C. Lithium hexamethyldisilazide (300 ml, 1 M in THF) was added in 2 h while keeping the reaction temperature below 5° C. Once addition was complete, stirring of the mixture was continued at 0-5° C. for 30 minutes. The mesylate from Example 1, dissolved in 20 ml of DMF, was then added to the reaction mixture in 10 minutes while keeping the internal temperature ≦0° C. Stirring of the mixture was continued at 0-5° C. for 2 h and then quenched by being poured into 400 ml of a saturated aqueous solution of $NH_4Cl$ and toluene (1/1). Once the phases had been separated, the organic phase was washed twice with 200 ml of brine and then concentrated under a vacuum down to a volume of 60 ml (92 A%, yield 80%).

$^1$H-NMR(CDCl$_3$): ppm 8.2-7 (m, 15 H); 3.95 (t, 1H); 3.8 (s, 3H); 3.2-2.8 (m, 2H); 2.7-2.2 (m, 4H); 2.2 (m, 2H); 0.5 (d, 4H);

EXAMPLE 3

[R-(E)]-2-[3-[3-[2-(7-chloro-2-quinolinyl)ethenyl] phenyl]-3-(2-benzyloxy-methyl)propyl)thiomethyl-cyclopropaneacetic acid hydrochloride (A4) (method 2)

60 ml of acetone and the solution in toluene of the product of Example 2 were introduced into a 500 ml flask equipped with a mechanical stirrer, a thermometer and a dropping funnel. A solution of gaseous HCl in toluene (60 ml) was added dropwise in 30 minutes at 15-20° C. A yellow precipitate is observed to form during the addition. The suspension was stirred at 20° C. for 30 minutes and then cooled to 5-10° C. for 1 h. The precipitate was filtered out under a vacuum and washed with 200 ml of a 2/1 mixture of acetone/toluene. The product was dried under a vacuum at 30° C. under a stream of $N_2$. Isolated yield 36.9 g; (99.1% A%; 80% yield) $^1$H-NMR (DMSO): ppm 8.9 (d, 1H); 8.4-8.1 (m, 4H); 7.8-7.1 (m, 10H); 3.95 (t, 1H); 3.85 (s, 3H); 3.1-2.6 (m, 2H); 2.25 (s, 2H); 2.1 (m, 2H); 1.8-1 (m, 2H); 0.0 (m, 4H).

EXAMPLE 3A

[R-(E)]-2-[3-[3-[2-(7-chloro-2-quinolinyl)ethenyl] phenyl]-3-(2-benzyloxy-methyl)propyl)thiomethyl-cyclopropaneacetic acid hydrochloride (A4) (method 3)

60 ml of acetone, 30 ml of toluene and the solution in toluene of the product of Example 2 were introduced into a 500 ml flask equipped with a mechanical stirrer, a thermometer and a dropping funnel. The solution was cooled to 5-10° C. and gaseous HCl was bubbled. through the solution. The mixture was then kept at 5-10° C. for 1 h, then the precipitate was filtered out and washed with 1/1 toluene/acetone (yield 80%; 99% A)

EXAMPLE 4

1-[1(R)-(3-(2-(7-chloro-2-quinolinyl)ethenyl)-phenyl)-3-(2-(1-hydroxy-1-methylethyl)phenyl)propyl) thiomethyl)-cyclopropaneacetic acid (VI)

16.4 g of $CeCl_3$ and 300 ml of THF were introduced into a 1 L flask equipped with a magnetic stirrer, a thermometer and a condenser. The suspension was refluxed for 4 h and then cooled to 0° C.; 85 ml of MeMgCl (0.25 moles; 3M in THF) were then added from a dropping funnel in 30 minutes while keeping the temperature below 0° C. Stirring of the mixture was continued at 0-5° C. for 40 minutes. 36.9 g of the methyl ester hydrochloride from Example 3, dissolved in 200 ml of THF, were added dropwise to the reaction mixture while keeping the internal temperature below 10° C. The mixture was stirred at 10° C. for 10 minutes and then poured into a 25% strength aqueous solution of NaOAc (200 ml) containing 1 ml of AcOH. The two phases were separated and the aqueous phase was extracted twice with 200 ml of i-PrOAc. The combined organic phases were concentrated under a vacuum at 20° C. down to a volume of 50 ml (43.4 g A% 99.6, yield 80%)

$^1$H-NMR(CDCl$_3$): ppm 0.45-0.55 (d, 4H); 1.58 (2 s, 6H); 2.15-2.65 (m, 6H); 2.85-2.95 (m, 1H); 3.2 (m, 1H); 3.95-4.0 (t, 1H); 7.05-8.05 (m, 15H).

EXAMPLE 5

1-[1(R)-(3-(2-(7-chloro-2-quinolinyl)ethenyl)-phenyl)-3-(2-(1-hydroxy-1-methylethyl)phenyl)propyl)thiomethyl)-cyclopropaneacetic acid sodium salt (I)

The solution of the acid from Example 4 was transferred into a 250 ml flask fitted with a mechanical stirrer and a thermometer. 1 equivalent of 1N NaOH was added and stirring of the mixture was continued at 20-25° C. for 30 minutes. The phases were separated and the aqueous phase was freeze-dried. 45 g of a light yellow solid were obtained in this manner (HPLC A%=99.5%).

$^1$H-NMR(CDCl$_3$): ppm 0.15-0.20 (d, 2H); 0.40 (d, 2H); 1.50 (s, 3H); 1.55 (s, 3H); 2.1-2.25 (m, 4H); 2.3-2.5 (dd, 2H); 2.70 (t, 1H); 3.25 (t, 1H); 4.5 (s, 1H) 6.95-8.0 (m, 15H).

EXAMPLE 6

1-[1(R)-(3-(2-(7-chloro-2-quinolinyl)ethenyl)-phenyl)-3-(2-(1-hydroxy-1-methylethyl)phenyl)propyl)thiomethyl)-cyclopropaneacetic acid (A3)

The acid hydrochloride from Example 3, 36.9 g (0.059 moles), was suspended in 185 ml of H$_2$O and 7.3 g of NaOAc were added to the suspension while stirring was continued. The mixture was stirred at ambient temperature for 1 h until dissolution was complete. The pH was adjusted to 5 with AcOH, 200 ml of isopropyl acetate were added and the phases were separated.

The organic phase was washed with 200 ml of brine and concentrated under a vacuum at 20° C. 34 g of a light yellow solid were obtained (A% 99.5; yield 98%).

EXAMPLE 7

1-[1(R)-(3-(2-( 7-chloro-2-quinolinyl)ethenyl)-phenyl)-3-(2-(1-hydroxy-1-methylethyl)phenyl)propyl)thiomethyl)-cyclopropaneacetic acid (VI)

16.4 g of CeCl$_3$ and 300 ml of THF were introduced into a 1 L flask equipped with a magnetic stirrer, a thermometer and a condenser. The suspension was refluxed for 4 h and then cooled to 0° C. 85 ml of MeMgCl (0.25 moles; 3M in THF) were added from a dropping funnel in 30 minutes while keeping the temperature below 0° C. Stirring of the mixture was continued at 0-5° C. for 40 minutes. 34 g of the methyl ester from Example 6, dissolved in 200 ml of THF, were added dropwise to the reaction mixture while keeping the internal temperature below 10° C. The mixture was stirred at 10° C. for 10 minutes and then poured into a 25% strength aqueous solution of NaOAc (200 ml) containing 1 ml of AcOH. The two phases were separated and the aqueous phase was extracted twice with 200 ml of isopropyl acetate. The combined organic phases were concentrated under a vacuum at 20° C. down to a volume of 50 ml (43.4 g, yield 80%).

EXAMPLE 8

1-[1(R)-(3-(2-(7-chloro-2-quinolinyl)ethenyl)-phenyl)-3-(2-(1-hydroxy-1-methylethyl)phenyl)propyl)thiomethyl)-cyclopropaneacetic acid sodium salt (I)

The solution of the acid from Example 7 was transferred into a 250 ml flask fitted with a mechanical stirrer and a thermometer. 1 equivalent of 1N NaOH was added and stirring of the mixture was continued at 20-25° C. for 30 minutes. The phases were separated and the aqueous phase was freeze-dried. 45 g of a light yellow solid were obtained in this manner (A% 99.5%).

EXAMPLE 9

Methyl [S-(E)]-2-[3-[3-[2-(7-chloro-2-quinolinyl)ethenyl]phenyl]-3-methanesulfonyloxy-propyl]benzoate (A2)

42 g (0.088 moles) of hydroxy ester monohydrate A$_1$ and 400 ml of toluene were introduced into a 1 L flask fitted with a mechanical stirrer, a thermometer and a distillation head. The suspension was heated to reflux and the water-toluene azeotropic mixture was removed by distillation at atmospheric pressure (200 ml). The solution was then cooled to 0-5° C.; DIPEA was added (33 ml, 0.194 moles) and the mesyl chloride (18.14 g, 0.158 moles) was finally added dropwise in 20 minutes while keeping the internal temperature ≦0° C. Once addition was complete, the solution was heated to 20° C. and was kept at this temperature for 2 h. Once this time had elapsed, the reaction mixture was poured into 500 ml of a saturated aqueous solution of NaHCO$_3$ kept at 5-10° C. The phases were separated and the organic phase was washed with a saturated solution of NaHCO$_3$ and then concentrated under a vacuum.

EXAMPLE 10

Methyl [S-(E)]-2-[3-[3-[2-(7-chloro-2-quinolinyl)ethenyl]phenyl]-3-methanesulfonyloxy-propyl]benzoate (A2)

20 g (0.042 moles) of hydroxy ether A$_1$ and 300 ml of toluene were introduced into a 500 ml flask fitted with a mechanical stirrer, a thermometer and a distillation head. The suspension was heated to reflux and the water-toluene azeotropic mixture was removed by distillation at atmospheric pressure. The residue was dissolved in 200 ml of methylene chloride and the solution was cooled to 0-5° C., 13 ml (0.092 moles) of TEA and 8.6 g (0.075 moles) of mesyl chloride were then added to the solution while keeping the internal temperature of the solution ≦0° C.

Once addition was complete, the solution was heated to 20° C. and kept at this temperature for 2 h. The mixture was then poured into 200 ml of a saturated aqueous solution of NaHCO$_3$ kept at 5-10° C. The phases were separated and the organic phase was washed with 200 ml of an aqueous solution of NaHCO$_3$ and then concentrated under a vacuum.

EXAMPLE 11

[R-(E)]-2-[3-[3-[2-(7-chloro-2-quinolinyl)ethenyl]phenyl]-3-(2-benzyloxy-methyl)propyl)thiomethyl-cyclopropaneacetic acid (A3)

10 g (0.068 moles) of 1-(mercaptomethyl)cyclopropaneacetic acid and 50 ml of THF were introduced under a stream of $N_2$ into a 500 ml flask fitted with a mechanical stirrer, a thermometer and a dropping funnel. The mixture was stirred at 20-25° C. for 5 minutes in order to ensure complete dissolution and was then cooled to 0-5° C. Lithium hexamethyldisilazide (143 ml, 1M solution in THF) was added to the reaction mixture in 1 h while keeping the internal temperature ≦5° C. Once addition was complete, stirring of the mixture was continued at 0-5° C. for 30 minutes.

The mesylate from Example 1, (16.6 g, 0.030 moles) dissolved in 30 ml of THF was then added to the reaction mixture while keeping the internal temperature ≦5° C. Once addition was complete, the mixture was kept at 0-5° C. for 4 h and was then poured into an aqueous solution of $NH_4Cl$ and toluene (1/1). The phases were separated and the organic phase was washed twice with 100 ml of brine and then concentrated under a vacuum. The product was obtained as a solid (32 g, 77 A%; 75% title, yield 75%).

EXAMPLE 12

[R-(E)]-2-[3-[3-[2-(7-chloro-2-quinolinyl)ethenyl]phenyl]-3-(2-benzyloxy-methyl)propyl)thiomethyl-cyclopropaneacetic acid hydrochloride (A4) (method 2)

The acid from Example 11 (32 g, 75% strength) was dissolved in 60 ml of acetone. A solution of HCl in toluene (60 ml) was added to the solution, which had been cooled to 5-10° C. A precipitate was observed to form during the addition. The suspension was kept at 5-10° C. for 1 h, then the precipitate was filtered out and washed with a 1/1 mixture of acetone/toluene. 22 g of a yellow solid were obtained (yield 88%; 90% A).

The invention claimed is:

1. A process for the preparation of Montelukast or pharmaceutically acceptable salts thereof comprising the following steps:
   (a) reaction of a compound A

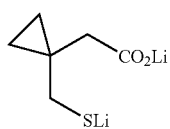

with a compound A2

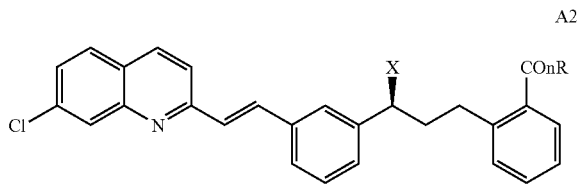

in which n varies between 1 and 2 and, when n is 1, R is methyl and, when n is 2, R is a $C_1$-$C_4$ alkyl or an aryl, and X is a leaving group, by nucleophilic substitution reactions in a dipolar aprotic solvent or in a mixture of dipolar aprotic solvent and ethereal solvent to yield the compound A3

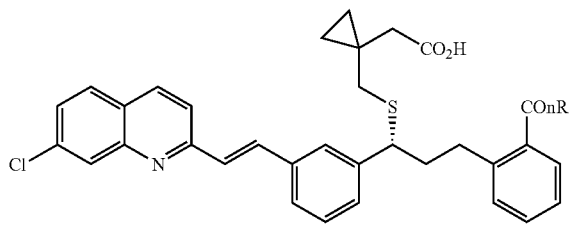

in which n and R have the above-stated meanings;
   (b) reaction of the compound A3 with an inorganic acid HY, in which Y is Cl, Br, I, and subsequent isolation of the resultant salt A4;

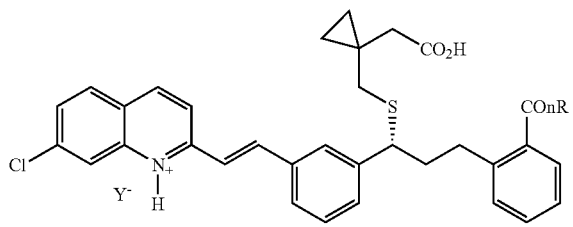

(c) optional conversion of the salt A4 into the compound A3;
   (d) methylation of the salt A4 and/or of the compound A3 to yield Montelukast.

2. A process according to claim 1, wherein the leaving group X is selected from the group consisting of $C_1$-$C_4$ alkylsulfonate and arylsulfonate.

3. A process according to claim 2, wherein said $C_1$-$C_4$ alkylsulfonate is methanesulfonate.

4. A process according to claim 1, wherein the dipolar aprotic solvent is selected from the group consisting DMF, DMA, DMSO, DMPU, and N-methylpyrrolidone.

5. A process according to claim 1, wherein the dipolar aprotic solvent is DMF and the ethereal solvent is THF.

6. A process according to claim 1, wherein step (a) is performed at a temperature of between 0° C. and 5° C.

7. A process according to claim 1, wherein said acid HY is selected from among HCl, HBr and HI.

8. A process according to claim 1, wherein step (b) is performed in an apolar or ketone solvent or in mixtures thereof.

9. A process according to claim 1, wherein step (b) is performed at a temperature of between 20° C. and 10° C.

10. A process according to claim 1, wherein step (d) is performed in an ethereal solvent.

11. A process according to claim 10, in which said ethereal solvent is THF.

12. A process according to claim 1, wherein step (d) is performed with MeMgCl.

13. A process according to claim 1, wherein step (d) is performed in the presence of cerium salts.

14. A process according to claim 13, wherein the cerium salt is CeCl$_3$.

15. A process according to claim 1, wherein step (d) is performed at a temperature of between 0 and 5° C.

16. A process according to claim 1, wherein the salt A4 is purified by crystallisation in an apolar or ketone solvent or in a mixture of the two.

17. A process according to claim 16, wherein said apolar solvent is toluene and/or said ketone solvent is acetone.

18. A process according to claim 1, wherein the conversion of the salt A4 into the compound A$_3$ is performed in an aqueous or aqueous alcoholic solvent.

19. A process according to claim 1, wherein the conversion of the salt A4 into the compound A$_3$ is performed at a pH of between 3 and 7.

20. A process according to claim 1, wherein the Montelukast is purified by pulping in an alcoholic solvent.

21. A process according to claim 20, wherein said alcoholic solvent is selected from among BuOH, s-BuOH, iso-BuOH.

22. A process according to claim 1, wherein the compound A is obtained by reaction between 1-(mercaptomethyl)cyclopropaneacetic acid and lithium hexamethyldisilazide.

23. A process according to claim 1, wherein the compound A2 is obtained by reaction between a compound A1,

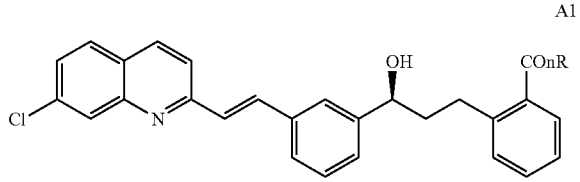

A1 in which n and R have the meanings stated in the preceding claims, and a C$_1$-C$_4$ alkylsulfonyl halide or an arylsulfonyl halide.

24. A process according to claim 23, wherein said C$_1$-C$_4$ alkylsulfonyl halide is mesyl chloride.

25. A process according to claim 23, wherein the compound A2 is obtained in an inert organic solvent in the presence of a tertiary amine.

26. A process according to claim 25, wherein the inert organic solvent is selected from among toluene and dichloromethane and/or the tertiary amine is selected from among triethylamine, diisopropylethylamine and dimethylaminopyridine.

27. A process according to claim 23, wherein the compound A2 is obtained at 0-20° C.

28. The compound of the formula

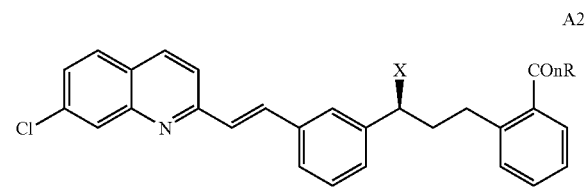

A2 wherein X n and R have the meanings stated in claim 1 and n is 2.

29. The compound of the formula

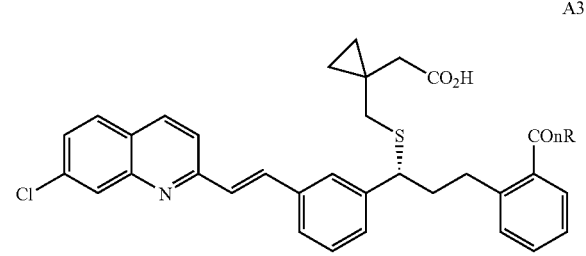

A3 wherein n is 2 and R have the meanings stated in claim 1.

30. The compound of the formula

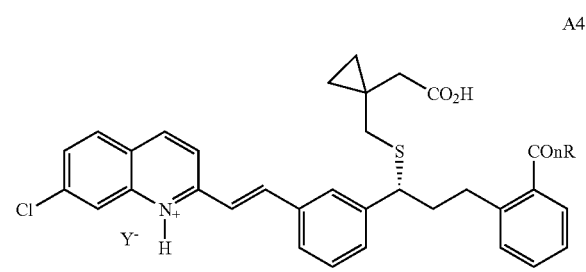

A4 wherein Y, n and R have the meanings stated in claim 1.

31. A process according to claim 8, wherein step (b) is performed in toluene/acetone.

* * * * *